(12) United States Patent
Chelen

(10) Patent No.: US 6,999,592 B2
(45) Date of Patent: Feb. 14, 2006

(54) TIME AND FREQUENCY WINDOWED POCKET CARDIAC STETHOSCOPE

(76) Inventor: William E. Chelen, 202 Parkview Dr., Pittsburgh, PA (US) 15236-4575

( * ) Notice: Subject to any disclaimer, the term of this patent is extended or adjusted under 35 U.S.C. 154(b) by 652 days.

(21) Appl. No.: 10/214,140

(22) Filed: Aug. 8, 2002

(65) Prior Publication Data
US 2004/0028236 A1    Feb. 12, 2004

(51) Int. Cl.
A61B 7/04    (2006.01)

(52) U.S. Cl. ........................................................ 381/67

(58) Field of Classification Search ............... 181/131; 381/67; 600/586, 559
See application file for complete search history.

(56) References Cited

U.S. PATENT DOCUMENTS

| | | | |
|---|---|---|---|
| 3,030,946 A * | 4/1962 | Richards ..................... 600/528 |
| 3,132,208 A | 5/1964 | Dymski et al. |
| 4,170,717 A | 10/1979 | Walshe |
| 4,438,772 A | 3/1984 | Slavin |
| 4,594,731 A | 6/1986 | Lewkowicz |
| 4,618,986 A | 10/1986 | Hower |
| 4,731,849 A | 3/1988 | Bloomfield, III |
| 4,792,145 A | 12/1988 | Eisenberg et al. |
| 4,821,327 A | 4/1989 | Furugard et al. |
| 5,003,605 A | 3/1991 | Phillipps et al. |
| 5,218,969 A | 6/1993 | Bredesen et al. |
| 5,557,681 A | 9/1996 | Thomasson |
| 5,602,924 A | 2/1997 | Durand et al. |
| 5,610,987 A | 3/1997 | Harley |
| 5,737,429 A | 4/1998 | Lee |
| 6,005,951 A | 12/1999 | Grasfield et al. |
| 6,512,830 B1 * | 1/2003 | Orten ........................... 381/67 |

* cited by examiner

Primary Examiner—Curtis Kuntz
Assistant Examiner—Alexander Jamal
(74) Attorney, Agent, or Firm—Stites & Harbison PLLC; Ross F. Hunt, Jr.

(57) ABSTRACT

A temporally and frequency controlled amplified cardiac stethoscope device is provided wherein frequency response selection is carried out by manually tuning two active filters thereby permitting user pass band (high and low frequency cutoff) selection. Simultaneously, the user is able to select a time window, or interval, of the audio output of the device for specific aural observation, to the exclusion of the remainder of cardiac cycle sounds. The device is miniaturized to permit transport in a clothing pocket and use in the clinic or at the bedside. The device is based upon electrocardiographic QRS complex/electronic Schmitt trigger synchronization of a sweep generator and comparator. The synchronization signal, in combination with manual user inputs, permits the control of digital/analog switching of on/off time intervals of a variable frequency response electronic stethoscope.

19 Claims, 4 Drawing Sheets

TIME AND FREQUENCY WINDOWED POCKET CARDIAC STETHOSCOPE

FIELD OF THE INVENTION

The present invention generally relates to stethoscopes and, more particularly, to an improved electronic cardiac stethoscope.

RELATED ART

The stethoscope has undergone many varieties of modification since its invention in 1819. These modifications have typically been attempts to increase the ability to detect and interpret the frequently subtle physiologic sounds originating in the thorax. Most of these modifications have occurred since the availability of small electronic components.

Numerous electronic stethoscopes have been proposed or developed over the past several decades. The predominant concept embodied by the majority of them has been one of controlled and variable amplification of physiologic sounds, e.g., U.S. Pat. No. 4,618,986, U.S. Pat. No. 4,170,717 and U.S. Pat. No. 4,438,772. Another concept in stethoscope improvement has been the effort in noise reduction or modification, e.g., U.S. Pat. No. 5,602,924 and U.S. Pat. No. 5,610,987. Another concept incorporated into electronic stethoscopes has been that of frequency response modification. Several means of shaping the frequency response have been demonstrated, e.g., U.S. Pat. No. 5,557,681, U.S. Pat. No. 4,821,327. U.S. Pat. No. 4,731,849 discloses a device which both shapes the frequency response and employs automatic gain control of a variable sound level. U.S. Pat. No. 4,792,145 discloses an electronic stethoscope that manipulates otherwise inaudible auscultated frequencies through the use of fast Fourier transformation and processing/translation.

U.S. Pat. No. 5,003,605 discloses an electrocardiographic system used to produce an acoustic timing signal to assist in the determination of expected timing of heart sounds. U.S. Pat. No. 4,594,731 discloses a device which employs electrocardiogram signals to time control the modulation of modified phonocardiogram auditory signals.

An attempt was made some time ago, as disclosed in U.S. Pat. No. 3,132,208, to provide an electronic stethoscope to enable "time-filtering" of physiologic sounds through the use of two adjustable transistor multi-vibrators which are periodically switched on or off. This system derives a control voltage from a prominent heart sound and with a 'three' rather than two lead electrocardiograph that does not permit compensation for varying body sizes and masses. The device suffers from potential false triggering of the time-filtering interval by the T-wave of the electrocardiogram or, potentially, a failure to trigger at all in an individual with low amplitude body surface potentials. This physically large device has no timing reference indicator or visible display and does not provide any frequency response processing or control. The device also requires numerous manual controls that can easily be mis-set and thus obviate correct functional control of the time-filtering in individuals with cardiac cycles of unusual length.

U.S. Pat. No. 6,005,951 discloses an unsynchronized clock/oscillator employed to select which components of both normal and abnormal heart sounds to amplify.

Recently, electronic stethoscopes have been disclosed that permit a visual display of auscultated sounds (U.S. Pat. No. 5,737,429) or permit automated analysis of auscultated sounds (U.S. Pat. No. 5,218,969).

In spite of the above, the art of stethoscopy remains a challenging one in large part due to the great effort and time required to acquire the concentration and mental time windowing necessary to isolate and identify sometimes very brief and low amplitude physiologic sounds.

SUMMARY OF THE INVENTION

The present invention obviates the need for much of the slowly acquired auscultatory skills referred to above by permitting the electronic selection of portions of the cardiac cycle to be amplified and tuned, and, subsequently, to be much more easily heard and identified. The invention also provides automatic compensation for cardiac size (by providing an automatic gain control to precisely determine triggering of each new cardiac cycle), and, potentially, the automatic determination of cardiac cycle length to further automate the auscultation process.

It is an object of the invention to provide an electronic stethoscope that permits the selection of a time window during the cardiac cycle for selective variable amplification.

Another object of the invention is to provide frequency windowing/band pass tuning of the phonocardiogram signal.

Another object of the invention is to provide automatic processing of all necessary functions, except that of the operator selected time and frequency parameters.

The invention relates, in general, to a miniaturized clinical device for frequency and time selective cardiac heart sound and peripheral vascular auscultation. The device permits detailed observation of single, individualized heart sounds or periods to the exclusion of all others, i.e., sounds such as normal heart sounds-S1 and S2, adventitious heart sounds, and murmurs (pre-systolic, systolic, and diastolic). The invention also permits selective detailed observation of ejection sounds, rubs, clicks, snaps, heart-sound splitting, and bruits of the, e.g., carotid, aortic, and femoral arteries, etc. The invention further permits frequency tuning of the selected time interval of sound, thereby enabling the selection of only relevant components of the phonocardiogram signal.)

Further features and advantages of the invention will be set forth in, or apparent from, the following detailed description of the preferred embodiments of the invention.

DETAILED DESCRIPTION OF THE PREFERRED EMBODIMENT

Figure 1:
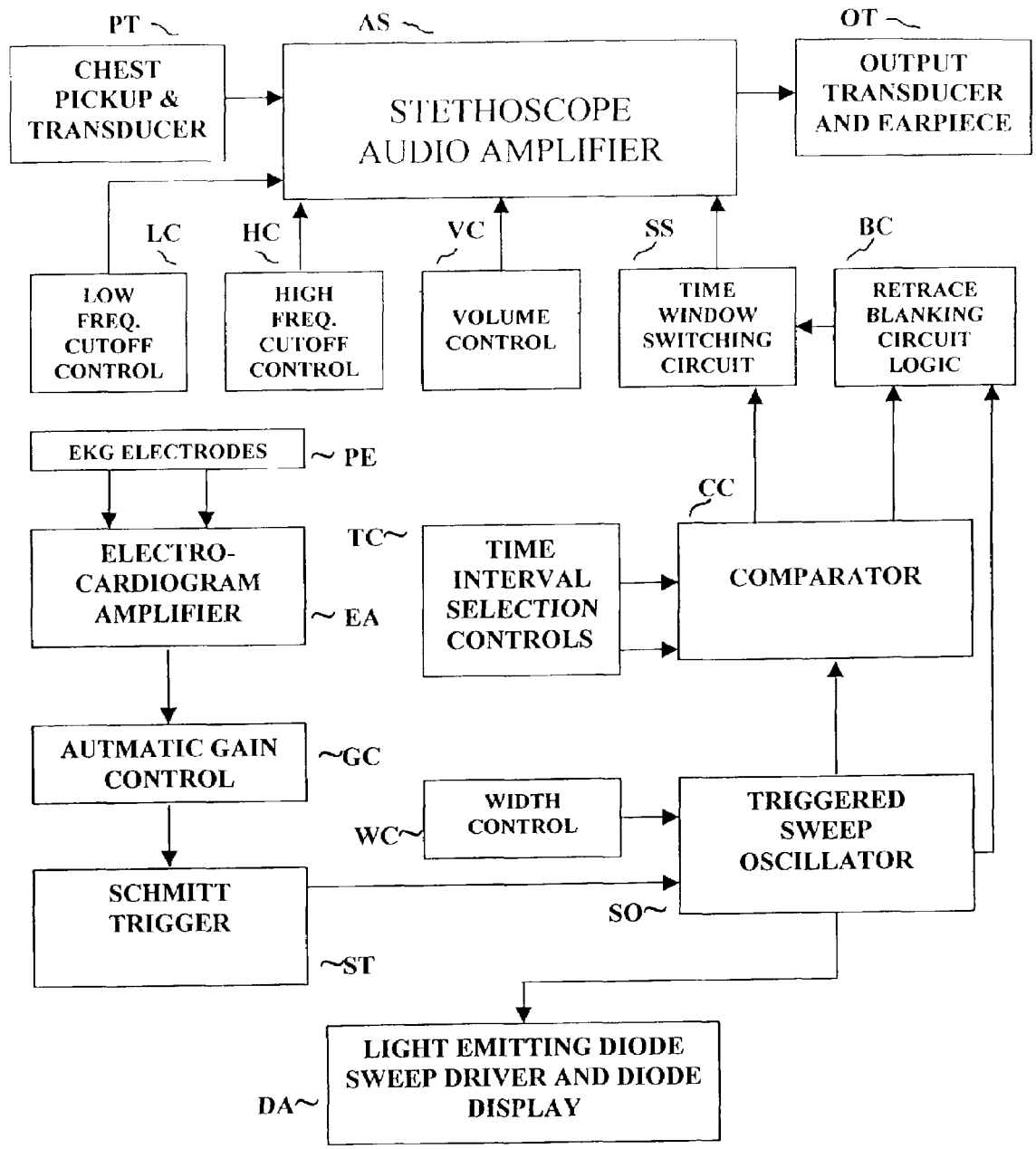
FIG. 1 is a block diagram of a preferred embodiment of the device of the invention.

In the preferred embodiment of the invention shown in FIG. 1, the device or system includes an amplified electronic frequency-band selective stethoscope AS, and an electrocardiogram amplifier EA. The latter is connected through an electrocardiogram automatic gain control circuit GC, and a Schmitt trigger ST, to a sawtooth ramp/sweep oscillator SO. The output of sweep oscillator SO form one input to a variable/adjustable comparator circuit CC as well as an input to a light emitting diode (LED) driver and display array DA and to a "retrace" noise suppression (blanking) circuit BC.

Comparator CC provides inputs an electronic time-window switching system or circuit SS and to blanking circuit BC.

The device of FIG. 1 also includes a chest pickup and transducer PT and an output transducer and earpiece OT. A low frequency cutoff control circuit LC, a high frequency cutoff control circuit HC, and a volume control circuit VC form inputs to stethoscope AS while skin surface EKG pickup electrodes PG produce the input signals for amplifier EA. Time interval selection controls TC are provided for comparators CC and a width control circuit WC is provided for sweep oscillator SO.

The operation of the device or system of FIG. 1 can be summarized as follows.

The frequency selective stethoscope audio amplifier AS is inputted as low level cardiovascular sounds by the pickup and transducer PT, and outputs its conditioned and controlled signal to the output transducer OT.

Within the frequency selective stethoscope AS are two adjustable variable frequency response 2-pole VCVS active filters (not shown). The low pass filter control LC permits the selection of a high frequency cutoff of from 100 to 3000 Hertz. The high pass frequency filter control HC permits the selection of a low frequency cutoff of from 20 to 300 Hertz. The volume control VC permits user selection of a wide volume range of the desired time interval selection for observation.

The electrocardiogram amplifier EA receives near millivolt cardiac skin surface potentials from electrodes PE. In this embodiment, amplifier EA consists of a 70 dB gain, 0.15 to 20 Hertz response system with an instrumentation amplifier front end.

The electrocardiogram automatic gain control circuit GC maintains a near constant 2 volt output for the Schmitt trigger ST in spite of a 4× range of variation in patient skin surface potentials.

The Schmitt trigger system ST converts a 0.8 volt or greater QRS complex into a "low" output to turn on and reset the sawtooth wave sweep oscillator SO.

The sawtooth wave sweep oscillator SO performs two functions. First, it drives the comparator circuits CC. The comparator circuits CC, with inputs from both the sawtooth oscillator SO and two user adjustable slide potentiometers TC, select the time interval/window of the cardiac cycle to be aurally observed by controlling an electronic switch SS.

Second, the sawtooth wave from oscillator SO drives the LED display system DA. The latter indicates to the user that the EKG complex has been captured, and indicates the duration of the sawtooth waveform so to permit user adjustment for a full width visual display through the use of the width control circuit WC.

Ancillary circuitry, including the retrace blanking circuit BC, using a series of logic gates, buffers, inverters and differentiators in parallel with the comparator output, maintains an open signal path (as needed) during the down-stroke of the sawtooth wave. This prevents an artifactual noise impulse from being added during selected off periods of the user selected time window.

The time window switching circuit SS is an electronic switch comprising a digitally controlled analog switch or gate, which opens and closes an audio signal path to alternately pass or block the electronic stethoscope audio signal.

Figure 2:
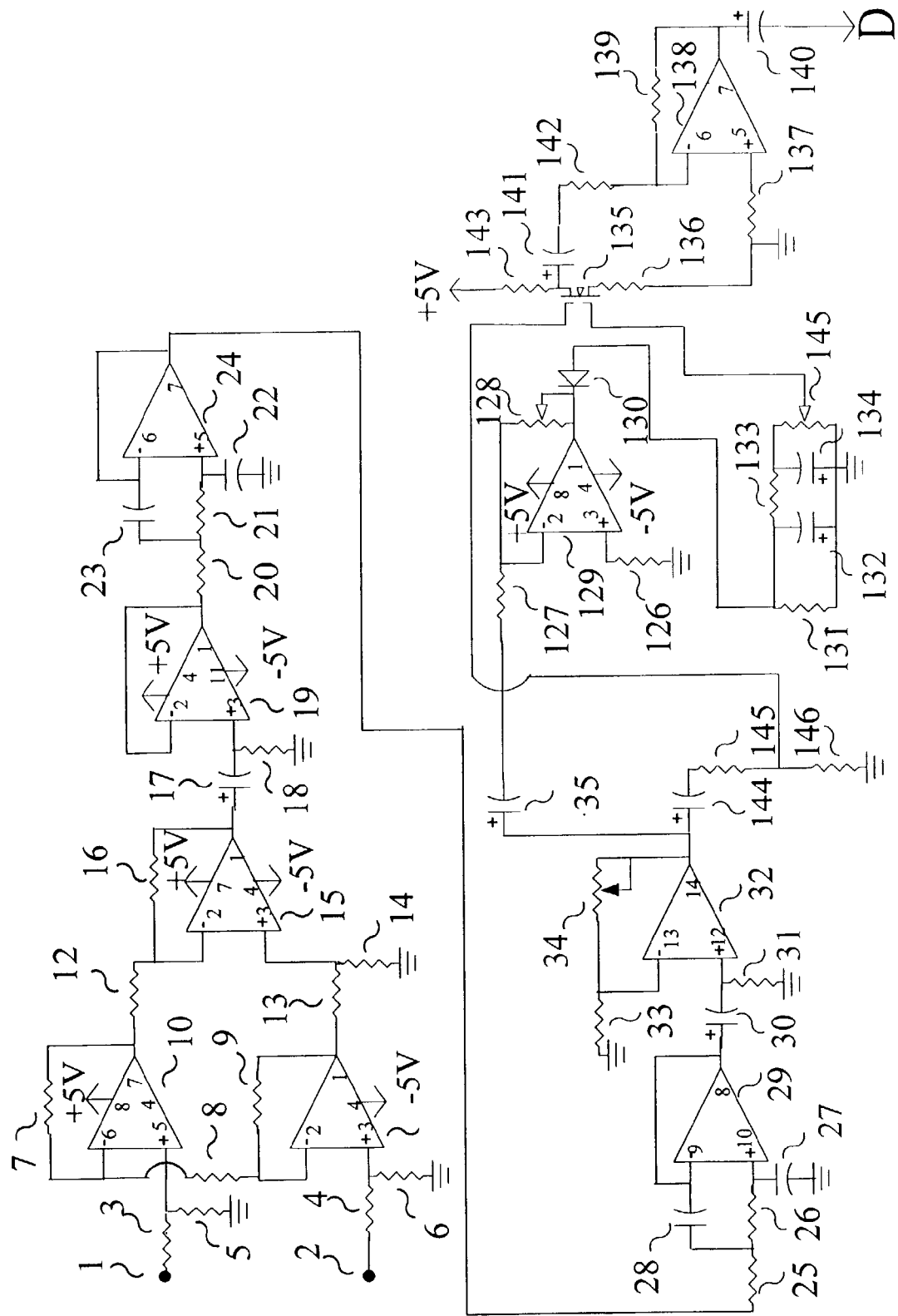
FIGS. 2 to 4, taken together, constitute a schematic circuit diagram of the device of FIG. 1, in accordance with a preferred embodiment thereof.
Figure 3:
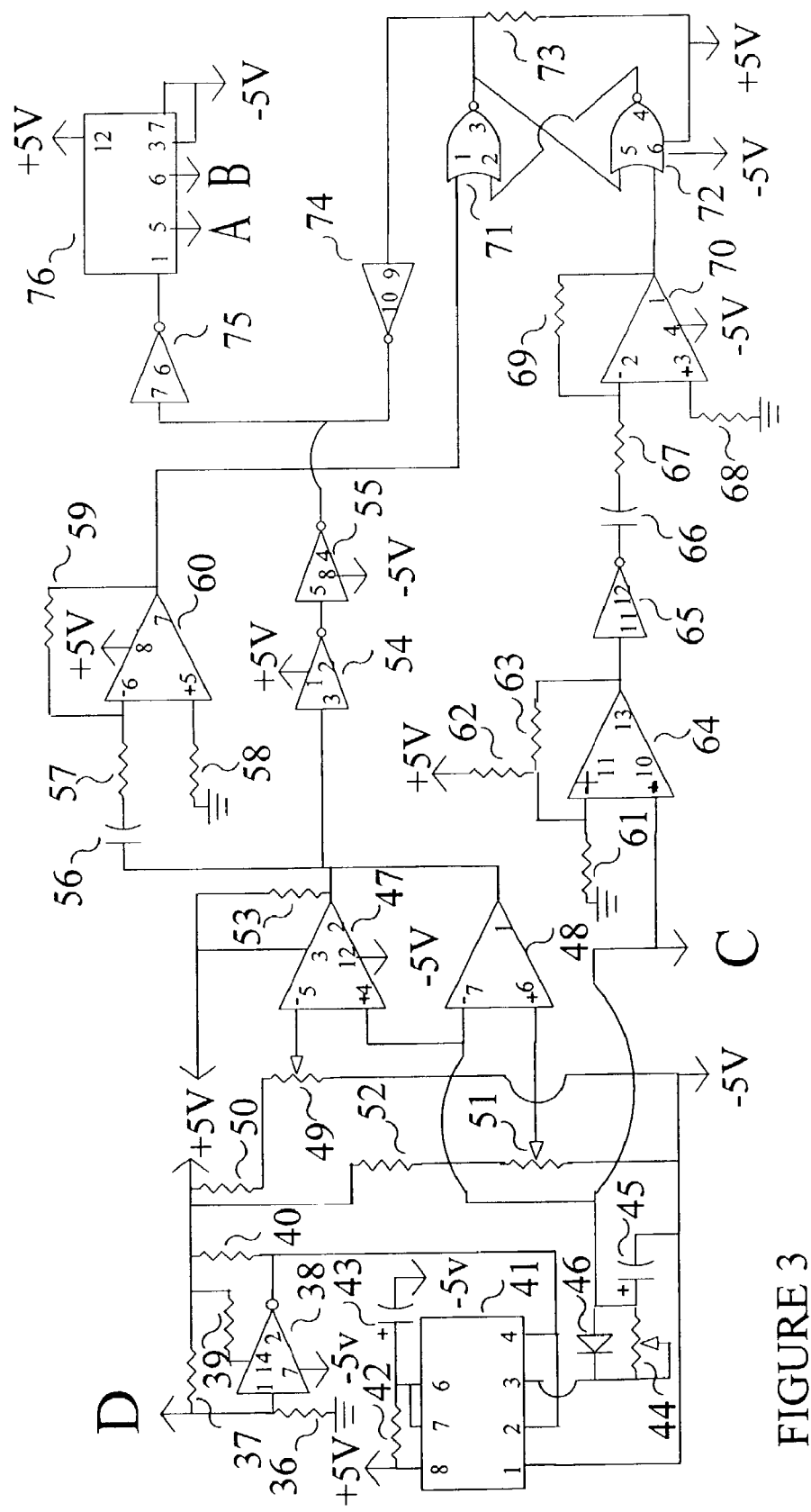
Figure 4:
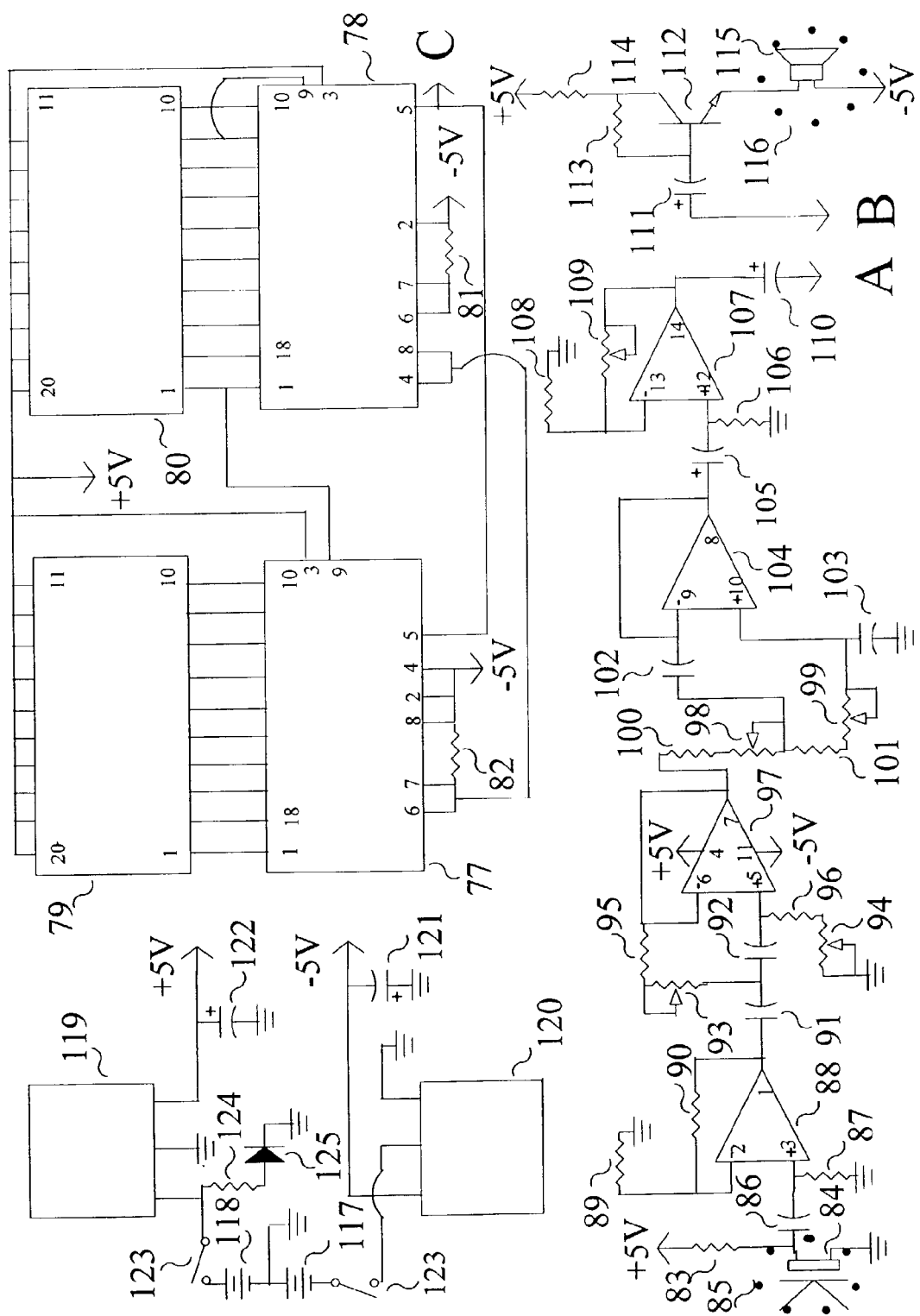

Referring now to FIGS. 2, 3 and 4, a schematic circuit diagram of a preferred implementation of the device is shown in these figures.

In FIG. 2, electrocardiographic lead I or II signals (from skin self-adhesive silver/silver chloride electrodes) are applied to operational amplifier inputs 1 and 2. The differential signal is passed through isolation resistors 3 and 4 to instrumentation amplifier integrated circuits 10 and 11 and through resistors 12 and 13 to integrated circuit 15. The ratios of resistors 7 to 8 and 16 to 12 determine the gain of the stages. Capacitor 17 and resistor 18 determine the low frequency cutoff of 0.15 Hertz and feed voltage follower integrated circuit 19.

This circuit feeds resistors 20 and 21, and capacitors 22 and 23, and unity gain operational amplifier 24, which comprise a low pass filter with a 20 Hertz cutoff. This filter feeds a second duplicate filter stage composed of resistors 25 and 26, capacitors 27 and 28, and unity gain integrated circuit 29. (The dual low pass filters, with a combined 12 dB per octave roll-off to suppress 60 Hertz ambient interference, permit EKG signal acquisition with only 2 input electrodes.) Capacitor 30 and resistor 31 form a 0.15 Hertz frequency cutoff high pass filter whose output is applied to the input of operational amplifier 32. Resistor 33 and potentiometer 34 determine the gain of the amplifier stage.

Capacitors 35 and 141 couple the pre-amplified electrocardiographic signal to integrated circuit 129 and a gate of MOSFET 135, respectively, of the automatic gain control (AGC) circuitry. The output of the AGC amplifier 129 is supplied to AGC rectifier diode 130 and filter capacitors and resistors, 131, 132, 133 and 134. This negative AGC voltage is applied, through potentiometer 145, to a gate of a N-channel MOSFET 135 and thereby reduces the stage gain with increasing AGC voltage. Conversely, with low level AGC voltages (secondary to reduced pre-amplified EKG voltages at the output of integrated circuit 32), the output from MOSFET 135 is enhanced. After amplification/inversion by integrated circuit 138, a nearly constant approximately 2 volt positive output pulse is supplied to capacitor 140 from each electrocardiogram QRS complex (to point D in FIGS. 2 and 3).

In FIG. 3, Capacitor 140 couples the conditioned and amplified electrocardiogram signal to integrated circuit 38, which is a Schmitt trigger corresponding to Schmitt trigger ST of FIG. 1. Resistors 36, 37, and 39 set the optimum bias for the trigger's activation. (When a signal exceeding approximately 1 volt positive, a QRS complex, appears at the input, the output switches from 5 volts to −5 volts.) This output is applied to the trigger circuit 38 and reset inputs of integrated circuit 41, which is a timer/oscillator generally corresponding to oscillator SO. The free-running period of the oscillator 41 is determined by resistor 42 and capacitor 43. (Each 5 to −5 volt transition initiates an oscillator cycle, and will begin/reset a new cycle.) Potentiometer 44, capacitor 45, and diode 46 transform the square wave oscillator output to a sawtooth waveform and permit the adjustment of its period/slope. The sawtooth waveform is applied simultaneously to a comparator formed by integrated circuits 47 and 48, 77 and 78 of FIG. 2, and comparator 64. Resistors 49 and 50, and 51 and 52 form voltage dividers to apply reference voltages to the integrated circuit comparators 47, 48. Resistors 49 and 51 are potentiometers whose values are manually set by the stethoscope's operator to choose the time window to aurally observe. Resistor 53 is the load resistor for the comparators 47, 48. The comparators' output is applied to the input of inverters 54 and 55 to provide comparator buffering/isolation. (A +5 volt/high output of the comparator/buffer represents the on period of the selected time window.)

The circuitry to prevent adventitious noise is as follows: The sawtooth waveform that was applied to the comparators 47, 48 is also applied to the inverting input of comparator 64.

As the down-sweep of the sawtooth reaches 0 volts, the comparator's output goes high to +5 volts. After inversion by inverter 65, a negative going pulse is differentiated by operational amplifier 70 to provide a brief positive pulse only when the sawtooth reaches zero. This pulse provides one input to NOR gate 72. Additionally, the output of comparators 47, 48 is applied to the input of differentiator 60. Differentiator 60 outputs a positive pulse only when the comparators' output drops from +5 volts toward zero volts. This pulse is applied to NOR gate 71 (which in conjunction with NOR gate 72, form a D-latch whose output is applied to inverter 74. The output of inverter 74, and the output of inverter 55 are applied to inverter 75.

The above series of inverters, differentiators, and NOR gates function in unison to switch off the analog switch (whenever the time window is not manually set to fully open) immediately when comparators 47, 48 begin to go negative and do not permit the switch to open until the sawtooth wave has re-initiated its cycle.

An example of the necessity of the noise suppression circuitry follows: A "time window" from ¼ to ¾ of, for example, a 1 second cardiac cycle is manually selected. As a result, the comparators' output would swing, at ¼ second, from 0 volts to 5 volts and turn on the audio amplifier. At ¾ second, the comparators' output would fall to 0 volts. However, to prevent a momentary re-triggering of a 5 volt output from the comparators (during the down-slope of the sawtooth waveform at the comparators input, a momentary positive pulse is outputted), this falling sawtooth edge generates a momentary positive pulse from differentiator 60 and triggers the D-latch, and through inverter 74, holds the input to inverter 75 low and keeps the analog switch off. However, to enable a new cardiac cycle to be enabled, comparator 64, enabled by the onset of a new sawtooth waveform, subsequently generates a brief positive pulse through differentiator 70 to trigger the D-latch to remove the low voltage from inverter 75. This low signal removal permits control of the analog switch to revert to comparators 47, 48 until the above cycle repeats.

The output of inverter 75 is applied to the input of analog switch 76. The output (switch) terminals of switch 76, A and B, are connected to the stethoscope audio amplifier signal path between capacitors 110 and capacitor 111 of FIG. 3 and pass the audio signal when the switch is closed.

As stated above, integrated circuits 77 and 78 of FIG. 4, also receive the sawtooth wave output. Both circuits are light emitting diode (LED) array drivers, which, in combination, sequentially illuminate a swept array of LEDs, 79 and 80, to display both EKG "capture" and the time interval through the cardiac cycle. (This permits the precision adjustment of the time window to be selected, and the manual adjustment of period of the sawtooth waveform.) Resistors 81 and 82 are used to select the voltage range for the sweep of the full diode array.

Also shown in FIG. 4 is the audio amplifier portion of the cardiac stethoscope. Resistor 83 supplies power to electret microphone 84, which is located behind the diaphragm portion of the chest-piece 85 of the "conventional" stethoscope head.

Capacitor 86 and resistor 87 provide coupling and low pass filtering at 20 Hertz for the output of the microphone. The signal is applied to the input of operational amplifier 88. Resistor 89 and resistor 90 determine the stage gain.

Capacitors 91 and 92 and potentiometers 93 and 94, and limit resistors 95 and 96 comprise a high pass filter which outputs to operational amplifier 97, connected as a unity gain stage.

Potentiometers 93 and 94 permit adjustment of the low frequency cutoff from between 20 and 1000 Hertz. This stage outputs to potentiometers 98 and 99, limit resistors 100 and 101, and capacitors 102 and 103 which comprise a low pass filter that outputs to unity gain operational amplifier 104.

Potentiometers 98 and 99 permit adjustment of the high frequency cutoff of the amplifier from between 200 and 3000 Hertz.

Amplifier 104 outputs to capacitor 105 and resistor 106, a 20 Hertz high pass filter. This filter outputs to operational amplifier 107. Resistor 108 and potentiometer 109 determine the gain of amplifier 107. Potentiometer 107 is the manually controlled volume control for the composite unit.

As stated above, the analog switch integrated circuit 76 is connected between capacitor 110 and coupling capacitor 111. This capacitor outputs to transistor 112, a power output stage.

Resistor 113 sets the proper operational bias for the stage. Resistor 114 is a current limiting resistor. Transistor 112 drives transducer 115. Transducer 115 converts the electrical output of transistor 112 to an acoustic/audio signal, which is directed into conventional stethoscope tubing/earpieces 116.

FIG. 4 also illustrates a dual polarity regulated power supply which is composed of two 9-volt batteries 117 and 118, a positive 5-volt regulator 119, a negative 5-volt regulator 120, and two filter capacitors 121 and 122, providing −5 and +5 volt supply voltages, a DPST switch and a LED indicator light.

Although the invention is obviously not limited to the specific implementation described above, typical values for the components shown in FIGS. 2, 3 and 4 are as follows:

1. patient skin surface electrode/input connector
2. patient skin surface electrode/input connector
3. 10K Ohms resistor
4. 10K Ohms resistor
5. 1 Meg Ohms resistor
6. 1 Meg Ohms resistor
7. 100K Ohms resistor
8. 18K Ohms resistor
9. 100K Ohms resistor
10. ½ LF353 integrated circuit operational amplifier
11. ½ LF353 integrated circuit operational amplifier
12. 27K Ohms resistor
13. 27K Ohms resistor
14. 220K Ohms resistor
15. LF356 integrated circuit operational amplifier
16. 220K Ohms resistor
17. 220 microfarads electrolytic capacitor
18. 4.7K Ohms resistor
19. ¼ MC3403 integrated circuit operational amplifier
20. 100K Ohms resistor
21. 330K Ohms resistor
22. 0.02 microfarad capacitor
23. 0.068 microfarad capacitor
24. ¼ MC3403 integrated circuit operational amplifier
25. 100K Ohms resistor
26. 330K Ohms resistor
27. 0.02 microfarad capacitor
28. 0.068 microfarad capacitor
29. ¼ MC3403 integrated circuit operational amplifier
30. 220 microfarads electrolytic capacitor
31. 4.7K Ohms resistor
32. ¼ MC3403 integrated circuit operational amplifier
33. 4.7K Ohms resistor
34. 100K Ohms potentiometer
35. 10 microfarads electrolytic capacitor 36. 2.2K Ohms resistor
37. 100K Ohms resistor
38. ⅙ 74LS14N Schmitt trigger
39. 220 Ohms resistor
40. 12K Ohms resistor
41. NE555 Oscillator/Timer integrated circuit
42. 200K Ohms potentiometer
43. 10 microfarads capacitor
44. 10K Ohms potentiometer
45. 47 microfarads capacitor
46. 1N34A germanium diode
47. ¼ LM339 quad comparator
48. ¼ LM339 quad comparator
49. 10K Ohms slide potentiometer
50. 27K Ohms resistor
51. 10K Ohms slide potentiometer
52. 27K Ohms resistor
53. 10K Ohms resistor
54. ⅙ CD4049 inverter
55. ⅙ CD4049 inverter
56. 0.33 microfarad capacitor
57. 10K Ohms resistor
58. 10K Ohms resistor
59. 100K Ohms resistor
60. ½MC33172 integrated circuit
61. 12K Ohms resistor
62. 220K Ohms resistor
63. 1 Meg Ohms resistor
64. ¼ LM339 quad comparator
65. ⅙ CD4049 inverter
66. 0.33 microfarad capacitor
67. 10K Ohms resistor
68. 10K Ohms resistor
69. 100K Ohms resistor
70. ½ MC33172 integrated circuit
71. ¼ CD4001M quad NOR gate
72. ¼ CD4001M quad NOR gate
73. 12K Ohms resistor
74. ⅙ CD4049 inverter
75. ⅙ CD4049 inverter
76. DG200ACJ analog switch integrated circuit
77. LM3914 LED array driver integrated circuit
78. LM3419 LED array driver integrated circuit
79. 10 segment LED display
80. 10 segment LED display
81. 1500 Ohms resistor
82. 2700 Ohms resistor
83. 4.7K Ohms resistor
84. electret microphone
85. stethoscope pickup hand-piece
86. 0.1 microfarad capacitor
87. 1000 Ohms resistor
88. ¼ MC3403 integrated circuit operational amplifier
89. 1000 Ohms resistor
90. 27K Ohms resistor
91. 0.1 microfarad capacitor
92. 0.1 microfarad capacitor
93. ½ dual 100K Ohms potentiometer
94. ½ dual 100K Ohms potentiometer
95. 2.2K Ohms resistor
96. 2.2K Ohms resistor
97. ¼ MC3403 integrated circuit operational amplifier
98. ½ dual 500K Ohms potentiometer
99. ½ dual 500K Ohms potentiometer
100. 3000 Ohm resistor
101. 3000 Ohm resistor
102. 0.005 microfarad capacitor
103. 0.01 microfarad capacitor
104. ¼ MC3403 integrated circuit operational amplifier
105. 10 microfarads capacitor
106. 1000 Ohms resistor
107. ¼ MC3403 integrated circuit operational amplifier
108. 1000 Ohms resistor
109. 100K Ohm potentiometer
110. 47 microfarads electrolytic capacitor
111. 47 microfarads electrolytic capacitor
112. 2N4904 transistor
113. 3.8K Ohms resistor
114. 100 Ohms resistor
115. 8 Ohms audio transducer
116. stethoscope tubing/earpieces
117. 9 Volt battery
118. 9 Volt battery
119. 7805 5 volt positive voltage regulator
120. 7905 5 volt negative voltage regulator
121. 1000 microfarads capacitor
122. 1000 microfarads capacitor
123. DPST switch
124. 1000 Ohms resistor
125. light emitting diode
126. 3000 Ohms resistor
127. 4700 Ohms resistor
128. 10K Ohms potentiometer
129. ½ LF353 integrated circuit operational amplifier
130. 1N34A diode
131. 15K Ohms resistor
132. 220 microfarads electrolytic capacitor
133. 15K Ohms resistor
134. 220 microfarads electrolytic capacitor
135. ECG221 dual gate MOSFET transistor
136. 15 Ohms resistor
137. 1500 Ohms resistor
138. ½ LF353 integrated circuit operational amplifier
139. 38K Ohms resistor
140. 1000 microfarads electrolytic capacitor
141. 1000 microfarads electrolytic capacitor
142. 1500 Ohms resistor
143. 1000 Ohms resistor
144. 470 microfarads electrolytic capacitor
145. 100K Ohms potentiometer
146. 3300 Ohms resistor
147. Misc: case, printed circuit, wiring, knobs, screws/hardware, solder, etc.

Although one preferred embodiment has been described above, it will be appreciated that many modifications and variations may be made in this embodiment. For example, the invention can employ LSI (large scale integration) integrated circuits incorporating all of or virtually all of the above components of the device/circuits (most likely using MOSFETs—metal oxide semiconductor field effect transistors—and FETs to minimize power consumption). Further, a LCD (liquid crystal display) can be used in place of LED display. In addition, a real time electrocardiographic display can be incorporated in parallel (simultaneously) with the sweep display on an LCD display. Further, an integrated miniaturized system (a LSI system as above) can be physically in line with stethoscope pickup and earpiece.

There can also be variations in the mechanism of the sawtooth generation circuit, e.g., a unijunction transistor circuit can be used, including one with second order compensation, and power supply variations, including miniature cell supplies, or single battery supplies, etc.

In addition, a single IC integrated instrumentation amplifier front end EKG amplifier can be used. Variations of the automatic gain control (a subcomponent IC of the LSI IC for the EKG amplifier) to obviate manual adjustment can be incorporated as can an automatic sweep width control for the sawtooth waveform generator components (to obviate manual adjustment).

It is, of course, also understood that equivalent semiconductors can be used in place of any or all of those specified in the preferred embodiment (e.g., a CD4066 quad analog switch integrated circuit can be substituted for the DG200ACJ analog switch). Further, a radio-telemetered EKG signal from the examinee to the time and frequency windowed electronic subunit can be employed to obviate/minimize motion artifacts to EKG pickup electrodes. Further, a radio-telemetered stethoscopic head audio transmitted to the time and frequency windowed electronic subunit can be used to obviate wiring inconvenience between the pickup and stethoscopic headphone unit. Further, additional stages of low pass filtering in the EKG amplifier can be provided to further reduce the 60 Hertz noise artifact.

Finally, while the invention has been described above relative to a preferred embodiment and specific variations and modifications thereof, it is also to be understood that still further variations and modifications may be made without departing from the scope and spirit of the invention.

What is claimed is:

1. A cardiac stethoscope device comprising:
    a stethoscope audio amplifier for producing an audio signal related to cardiac heart sounds produced by a patient, said audio amplifier including first and second manually adjustable filters for enabling selection of a frequency response pass band;
    an electrocardiogram amplifier for amplifying skin surface potentials of the patient and for producing a corresponding output signal;
    signal processing means for processing said output signal to produce a synchronization control signal for controlling operation of said stethoscope audio amplifier;
    switching means for, responsive to said synchronization signal and to a user controlled time interval selection input, selectively controlling blocking and passing of said audio signal produced by said stethoscope audio amplifier so as to provide a time window for aural observation of the heart sounds to the exclusion of the remaining cardiac heart sounds, said signal processing means including:
        a sweep oscillator for producing an output signal having a sawtooth waveform; and
        an electronic trigger circuit, connected to said electrocardiogram amplifier and to said sweep oscillator, for controlling resetting of said sweep oscillator based on the output of said electrocardiogram amplifier.

2. A device as claimed in claim 1 further comprising an adjustable comparator, connected to said sweep oscillator and including adjustable time interval controls, for producing a control signal for controlling said switching means.

3. A device as claimed in claim 1 further comprising display means connected to said sweep oscillator for displaying the output signal produced by said sweep oscillator.

4. A device as claimed in claim 2 further comprising a logic control blanking circuit, connected to said comparator and said sweep oscillator and to said switching means, for controlling switching of said switching means to maintain an open signal path, as needed, during a down-stroke portion of said sawtooth waveform.

5. A device as claimed in claim 1 further comprising a high frequency cutoff control circuit and a low frequency cutoff control circuit, both connected to said audio amplifier, for controlling the cutoff frequencies of said first and second adjustable filters.

6. A device as claimed in claim 1 further comprising an automatic gain control circuit connected between said electrocardiogram amplifier and said electronic trigger circuit.

7. A device as claimed in claim 3 wherein said display means comprises a light emitting diode sweep driver and a light emitting diode display.

8. A device as claimed in claim 4 wherein said electronic trigger circuit comprises a Schmitt trigger.

9. A cardiac stethoscope device comprising:
    a stethoscope audio amplifier, including first and second adjustable filters, for producing an audio signal related to cardiac heart sounds of a patient;
    an electrocardiogram amplifier for sensing and amplifying skin surface potentials and producing a corresponding output;
    a sweep oscillator for producing a sawtooth waveform output signal;
    an electronic trigger circuit, connected to said electrocardiogram amplifier and to said sweep oscillator, for controlling resetting of said oscillator based on the output of said electrocardiogram amplifier;
    display means connected to said oscillator for displaying said output signal produced by oscillator;
    an adjustable comparator, connected to said oscillator and including adjustable time interval controls, for producing a control signal used in controlling a time window for aural observation of the cardiac cycle of the patient; and
    a time window switching circuit, connected to said audio amplifier, for responsive to said control signal produced by said comparator, for passing or blocking the audio signal produced by said audio amplifier.

10. A device as claimed in claim 9 further comprising a chest pickup and transducer device, connected to said stethoscope audio amplifier, for producing said heart sounds.

11. A device as claimed in claim 9 further comprising a high frequency cutoff control circuit and a low frequency cutoff control circuit, both connected to said audio amplifier, for controlling the cutoff frequencies of said first and second adjustable filters.

12. A device as claimed in claim 9 further comprising a volume control circuit connected to said stethoscope audio amplifier.

13. A device as claimed in claim 9 further comprising an output transducer and ear piece connected to said stethoscope audio amplifier.

14. A device as claimed in claim 9 further comprising a logic control blanking circuit, connected to said comparator and said sweep oscillator and also to said time window switching circuit, for controlling switching of said switching circuit to maintain an open signal path, as needed, during a down-stroke portion of said sawtooth output signal.

15. A device as claimed in claim 9 further comprising a width control circuit connected to said sweep oscillator for controlling the period of said sawtooth output signal.

16. A device as claimed in claim 9 further comprising an automatic gain control circuit connected between said electrocardiogram amplifier and said electronic trigger circuit.

17. A device as claimed in claim 9 wherein said display means comprises a light emitting diode sweep driver and a light emitting diode display.

18. A device as claimed in claim 9 wherein said electronic trigger comprises a Schmitt trigger.

19. A device as claimed in claim 9 further comprising a plurality of EKG electrodes connected to said electrocardiogram amplifier for producing signals corresponding to said skin surface potentials.

* * * * *